United States Patent [19]
Vidrine et al.

[11] Patent Number: 6,018,677
[45] Date of Patent: Jan. 25, 2000

[54] HEART RATE MONITOR AND METHOD

[75] Inventors: Drouét Warren Vidrine, San Juan Capistrano, Calif.; Jack Gordon Kisslinger, Madison, Wis.; Joseph Michael Brown, Lake Forest, Calif.

[73] Assignee: Tectrix Fitness Equipment, Inc., Irvine, Calif.

[21] Appl. No.: 08/978,185

[22] Filed: Nov. 25, 1997

[51] Int. Cl.[7] ....................................... A61B 5/04
[52] U.S. Cl. ............................................... 600/520
[58] Field of Search ................................. 600/519, 520, 600/521; 428/901

[56]  References Cited

U.S. PATENT DOCUMENTS 5,243,993   9/1993   Alexander et al. ..................... 600/520

*Primary Examiner*—Scott M. Getzow
*Attorney, Agent, or Firm*—Myers, Dawes & Andras LLP

[57] ABSTRACT

A novel system and method for measuring and monitoring heart rate during exercise is disclosed. A near-real-time heart rate is obtained by extracting an electrocardiographic signal via electrically conductive handgrips, severely reducing the bandwidth of the signal using analog filtering, and then applying sophisticated digital correlation and logic techniques to extract the heart rate. The severe reduction of information content accomplished by the analog filter allows sophisticated digital treatment of the remaining signal by inexpensive digital processing means. In the present embodiment, a mass-produced general-purpose single-chip 8-bit microprocessor is adequate to accomplish all the required digitization and calculations.

22 Claims, 14 Drawing Sheets

HEART RATE MONITOR AND METHOD

This invention relates to the use of certain electronic and algorithmic methods to electrocardiographically recognize and non-invasively measure human heart rate during exercise. This invention has particular utility in measuring heart rate robustly and accurately with inexpensive electronics, in the presence of the strong static, triboelectric, and myoelectric impulses associated with physical exercise.

BACKGROUND OF THE INVENTION

In general, the incorporation of heart rate monitors into exercise equipment has been desirable since the beginnings of the commercial exercise equipment industry. Heart rate has traditionally been used as a standard measure of physical condition and exercise intensity, and medical prescriptions often specify a target heart rate to be maintained during the prescribed exercise. However, traditional sonometric techniques require interruption of exercise, and catheter-based manometric measurements have proved to be too invasive for general use. Oxymetric measurements using earlobe clips and electrocardiographic measurements using conventional saline gel electrodes have not been well received by exercise equipment users. Other minimally invasive techniques such as wrist-strap sonography have proven to be susceptible to interference during strenuous exercise. Note that the definition of the term "invasive" differs slightly from its use in medical procedures in that methods which require earlobe clips, shaving of skin areas, the application of adhesive pads to skin, or even the placement of a strap underneath clothing are considered psychologically invasive of a user's personal space.

PREVIOUS TECHNIQUES

The first routinely useful exercise heart rate monitor was a chest strap system, which allowed electrocardiographic heart rate measurement without the use of discrete skin electrodes or messy saline gels. The high-quality electrocardiographic signal available from a chest-strap's array of embedded skin electrodes allows reliable heart rate measurement with an extremely simple detection circuit. However, this monitor was still not widely accepted because it requires the donning and wearing of a chest strap underneath the shirt during exercise.

Recently, heart rate monitors utilizing conductive handgrips as electrodes have begun to be incorporated into exercise equipment. These monitors have generally had heart rate detection circuits which fall into two classes: (a) analog comparator detectors which are susceptible to myoelectrical noise and individual variations in cardiac signal output, and are mainly useful for determining heart-rate during hiatus in exercise, and (b) digital detectors which rely on autocorrelation techniques and utilize expensive high-bandwidth analog-to-digital converters and dedicated digital signal processing hardware. As the name implies, autocorrelation utilizes the incoming signal itself to generate the model dynamically.

THE CHARACTERISTICS OF HANDGRIP ELECTRODE DETECTION

The electrocardiographic impulse generated as part of each heartbeat polarizes the human body, and can be detected by electrodes in contact with two different parts of the body. In the average person, the strongest vector direction of this polarization is downwards and somewhat leftwards within the torso. For instance, a near-maximum electrocardiographic signal can be obtained by placing electrodes on the right shoulder and left hip. Most of the population exhibits a useful amount of transverse (leftwards) vector component, and the use of handgrip electrodes for heart rate measurement depends on this.

The measurement of the electrocardiographic signal via handgrips imposes several difficulties because of the increased interference compared with measurement at the torso. First, the signal is weak because it lacks its strongest (vertical) vector component. Second, muscle activity during exercise produces strong, sharp myoelectrical signals that seriously contaminate the electrocardiographic signal during exercise. Third, the electrical contact via the skin is inferior because it depends on the variable contact and pressure of the hand on the grip, is mediated by a variable quantity of conducting electrolyte (sweat), and is made with an unusually thick and insulative portion of the skin surface (the palm of the hand). Fourth, triboelectrical effects produce noise and other interference with the signal during exercise. Fifth, electrochemical polarization effects at the electrode surface can produce noise and insulative interference.

SUMMARY OF THE INVENTION

In its broadest aspect, the present invention comprises a novel method and apparatus for measuring heart rate during exercise. Briefly, a near-real-time heart rate is obtained by extracting an electrocardiographic signal via electrically conductive handgrips, severely reducing the bandwidth of the signal using analog filtering, and then applying sophisticated digital correlation and logic techniques to extract the heart rate. The severe reduction of information content accomplished by the analog filter allows sophisticated digital treatment of the remaining signal by inexpensive digital processing means. In the present embodiment, a mass-produced general-purpose single-chip 8-bit microprocessor is adequate to accomplish all the required digitization and calculations.

Correlation of the time-varying electrocardiographic signal with a reference electrocardiographic heartbeat signal pattern (the "template") allows the selection of electrocardiographic events in the presence of considerable noise. This process differs from autocorrelation in that the incoming signal does not affect the template. In distinction, autocorrelation utilizes the incoming signal itself to generate the template, potentially tailoring the template to the personal characteristics of the particular person generating the incoming signal, but potentially contaminating the template with ambient noise or extraneous pseudo-periodic phenomena and risking the correlative integrity of the algorithm. Realizing the mathematical operation of template correlation in real-time measurement generally requires considerable computing power and/or dedicated digital signal processing electronics. However, the severe reduction in information content produced by the analog filter allows sophisticated mathematical treatment of this preconditioned signal with an inexpensive, limited-speed, general-purpose microprocessor, while retaining enough processor time to allow multivalent heuristic logic decisions based on the partially processed information.

The approach of severely limiting bandwidth by analog filtering allows a further novel improvement. Myoelectrical impulses generally occur over a much shorter time-scale than electrocardiographic impulses, but myoelectrical impulses contain enough energy to contribute considerable noise within the low-frequency spectrum, so simple filtering may not adequately attenuate them. Fast-recovery clipping of the input signal to reduce the energy of individual myoelectrical impulses, followed by the low-frequency filtering, retains the electrocardiographic information while reducing both the myoelectrical contribution and the total information content.

Another novel improvement utilizes slack time in the programmable microprocessor to perform logical filtering on the correlated signal. In the presence of exercise activity and its consequent interference with the electrocardiographic signal, some heartbeat events will be masked by myoelectrical noise, and myoelectrical noise will also sometimes produce false-heartbeat-like features in the electrocardiographic signal. Instead of simply utilizing correlation maxima as heartbeat indicators, a more robust heart rate is obtained by maintaining a parameterized list of candidate heartbeat intervals in a ring buffer, then utilizing them to construct a most-probable heart rate. One advantage of this approach is that previously evaluated heartbeat interval candidates are continually re-evaluated in light of further events, and accidental correlations can be rescinded. Another advantage is that missing heartbeats and false heartbeats are recognized and excluded from the result. Another advantage is that heart interval events which are highly qualified on the basis of parameters such as intensity, lack of inter-beat noise, and resemblance to neighboring events, can be logically weighted more highly than candidate events lacking these qualities.

Complete systems have additional elements which may not be claimed in this patent, but which are necessary or desirable for operation. As an example, one complete embodiment of the invented system consists of (a) electrodes designed to be touched with left and right fingers, hands, or arms, so that a person's heart-rate can be non-invasively and comfortably monitored; (b) a signal transmission system which rejects ambient electromagnetic noise, over-voltage clipping and static protection circuitry; (c) analog amplification, filtering, and signal clipping to reject common-mode noise such as static and triboelectric contributions, and restrict the information content to a type and range favorable for detecting the electrocardiographic signal in the presence of myoelectrical activity and other noise, while limiting the amount of digital calculation necessary to monitor heart-rate; (d) an active method for detecting whether a human is touching the electrodes by measurement of interelectrode impedance; (e) a heart-rate extraction algorithm utilizing wavelet correlation, including multiple concurrent algorithmic means for extracting candidate heart-rates; (f) a logical arbitrator for choosing among the candidate heart-rates and assessing their validities; (g) a processing/display system capable of displaying heart-rate and/or utilizing heart-rate information to modulate an exercise program; (h) diagnostic means including self-test hardware and firmware, (i) a bi-directional port for transferring detailed information about the operation of the monitor and its algorithm; and (j) power supply and information transfer means capable of powering the heart-rate monitor and transferring information while maintaining electrical isolation for physiological safety and static isolation, allowing the use of only two bio-potential sensing electrodes. The patent claims cover some original aspects and original combinations of the above components. The following is the description of a current embodiment of the invention.

BRIEF DESCRIPTION OF THE DRAWINGS

FIG. 9, the Interrupt Handler, is the most complex. It is running the ADC, computing dot products, etc. concurrently with other operations.

DETAILED DESCRIPTION OF SPECIFIC EMBODIMENTS

Figure 1:
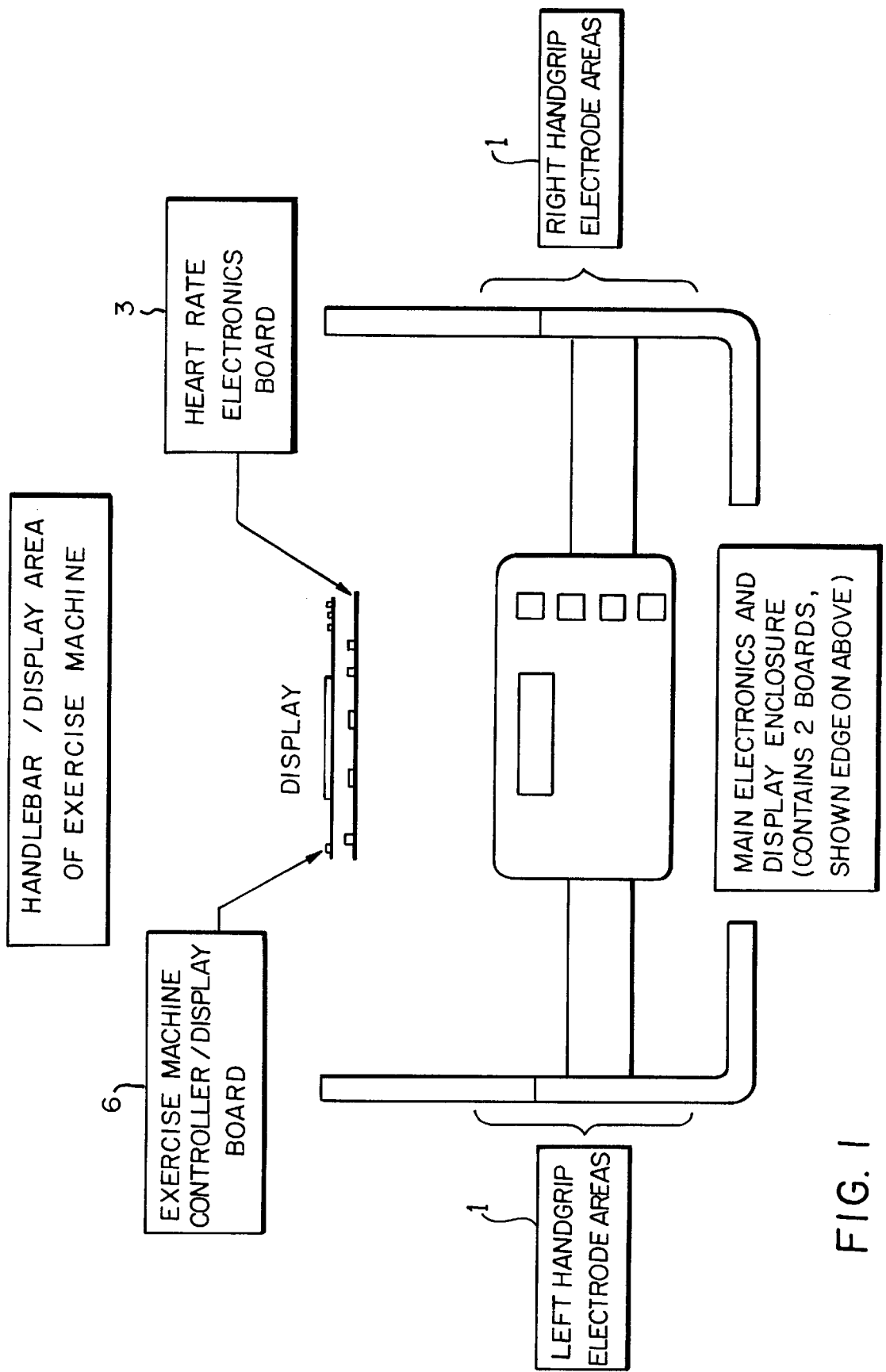
FIG. 1 is an example of the physical layout of a representative embodiment.

FIG. 1 shows the handgrip electrodes 1, which are arranged conveniently such that the user will tend to naturally place his hands on these electrodes during exercise. When the user's hands are contacting the respective electrodes, an electrocardiographic signal is present between the two electrodes. An electrical connection is made between each electrode and the heart rate monitor electronics 3. The characteristic electrical signal produced by the body during each heartbeat, or electrocardiographic heartbeat signature 4 (the electrocardiogram, or ECG) is composed of a series of characteristic signals, the largest grouping of which are termed the "QRS complex", or "QRS" 5 in medical practice. For details, refer to "Biomedical Digital Signal Processing", Willis J. Tompkins, editor, p. 32, FIG. 2.8, Prentice Hall, N.J., 1993. In one preferred embodiment, multiple, physically discontinuous electrode areas are supplied for each electrode, such that the user has a choice of hand positions during exercise. Finally a data link connection is made between the heart rate electronics board 3 and the exercise machine controller/display board 6.

Figure 2:
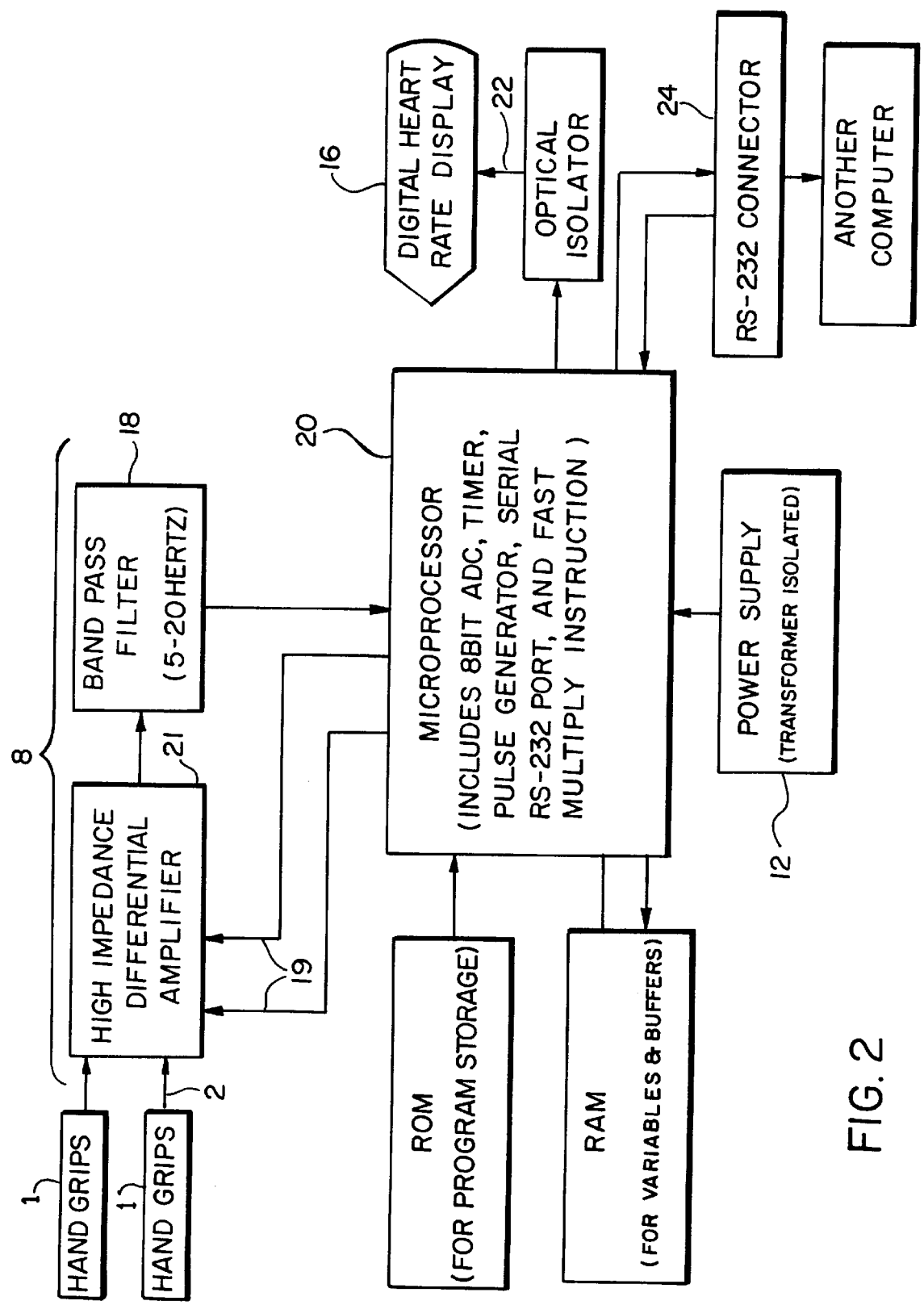
FIG. 2 is a block diagram of the hardware used for signal extraction.
Figure 3A:
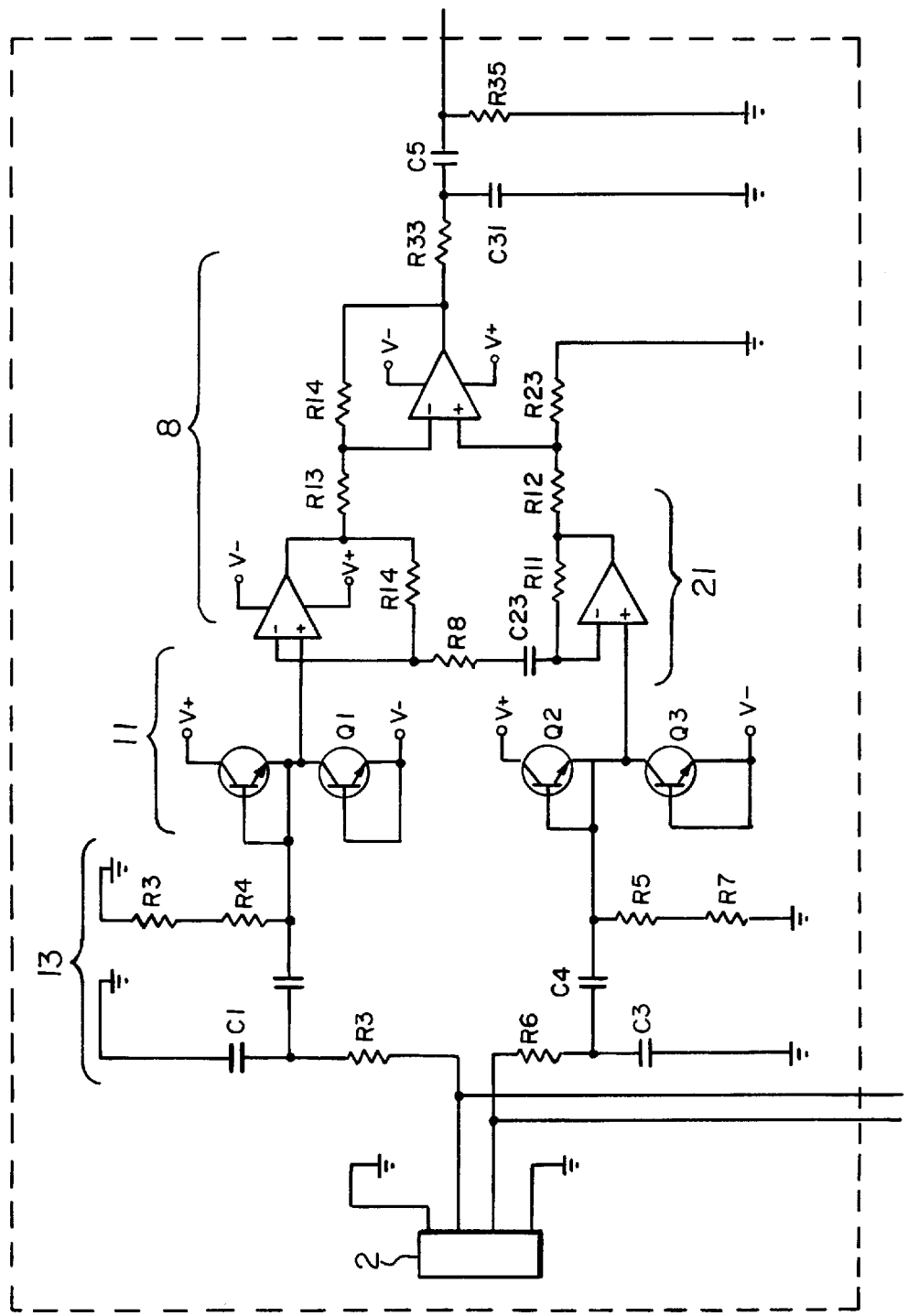
FIG. 3 (3a, 3b, 3c, 3d, 3e and 3f) is a schematic of the electronics used for this purpose.
Figure 3B:
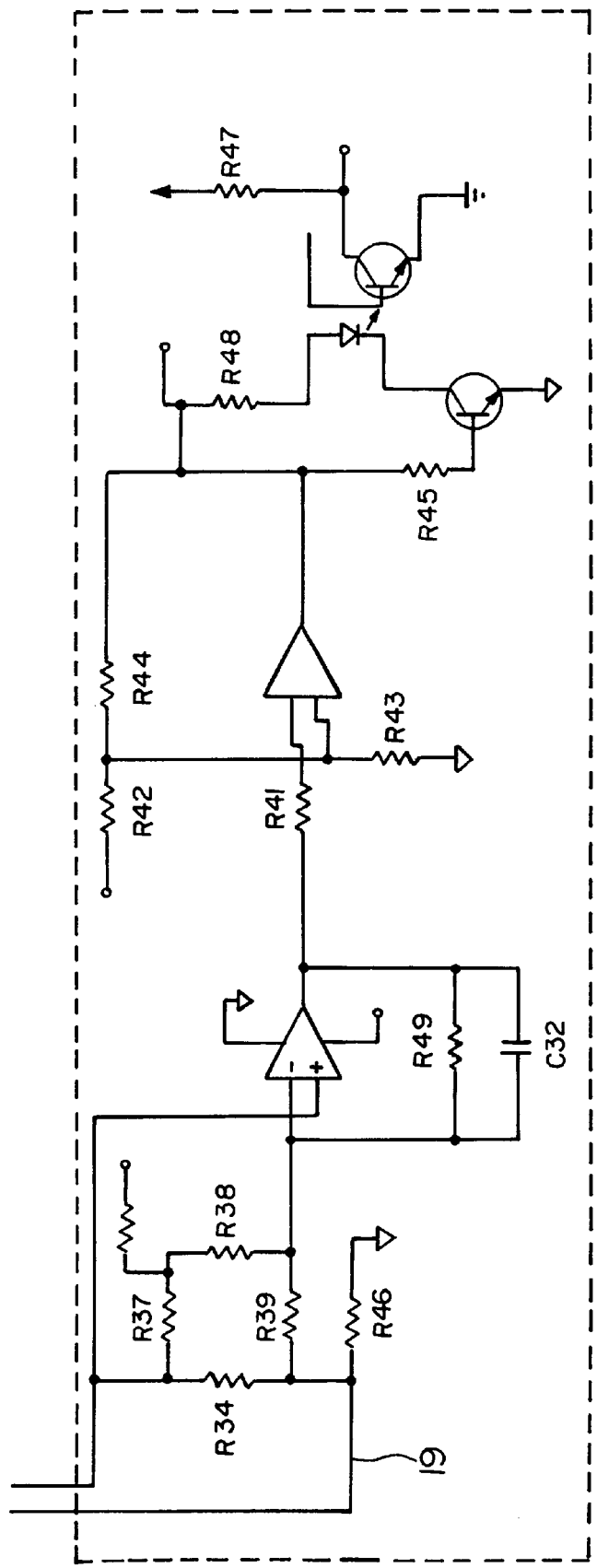
Figure 3C:
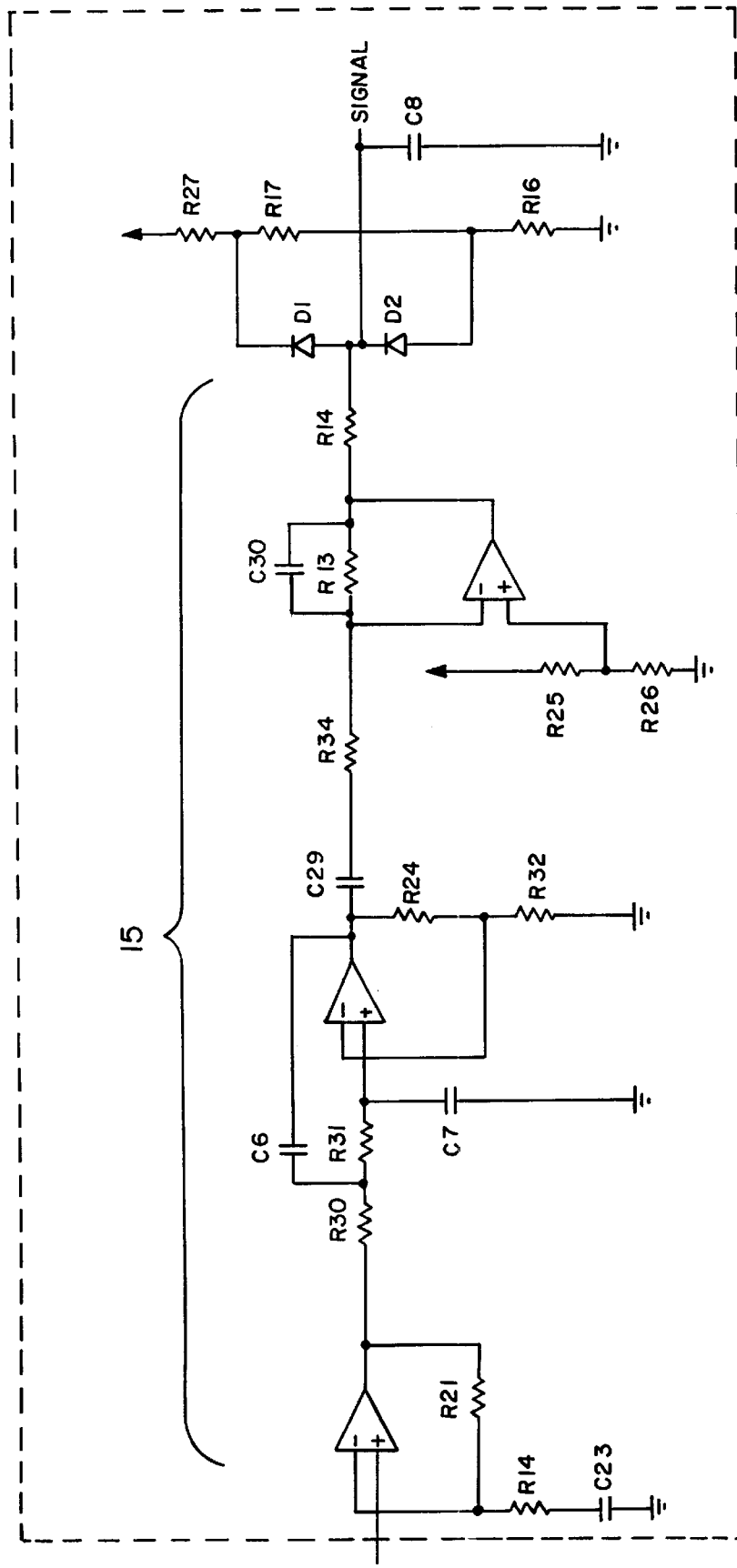
Figure 3D:
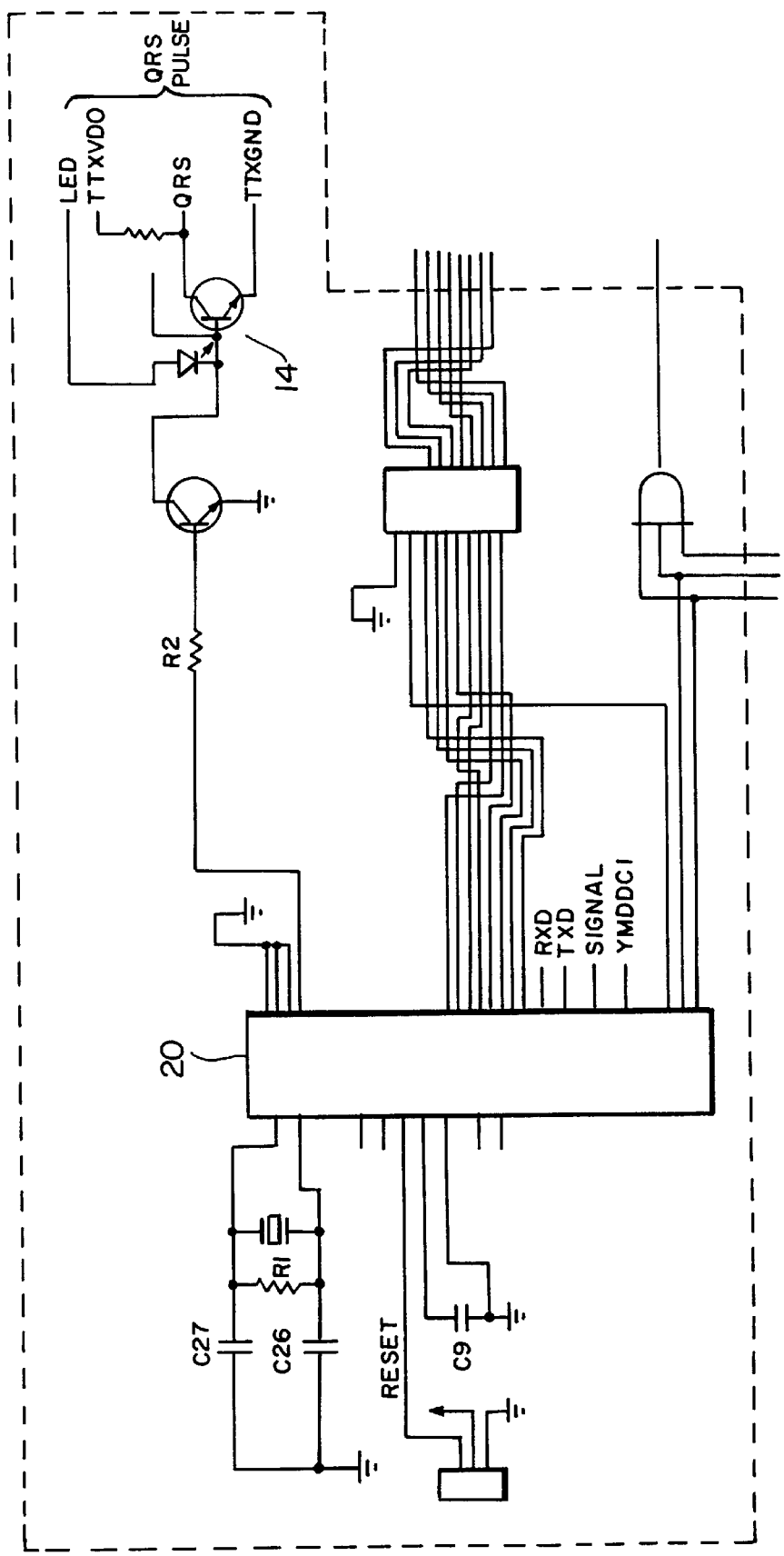
Figure 3E:
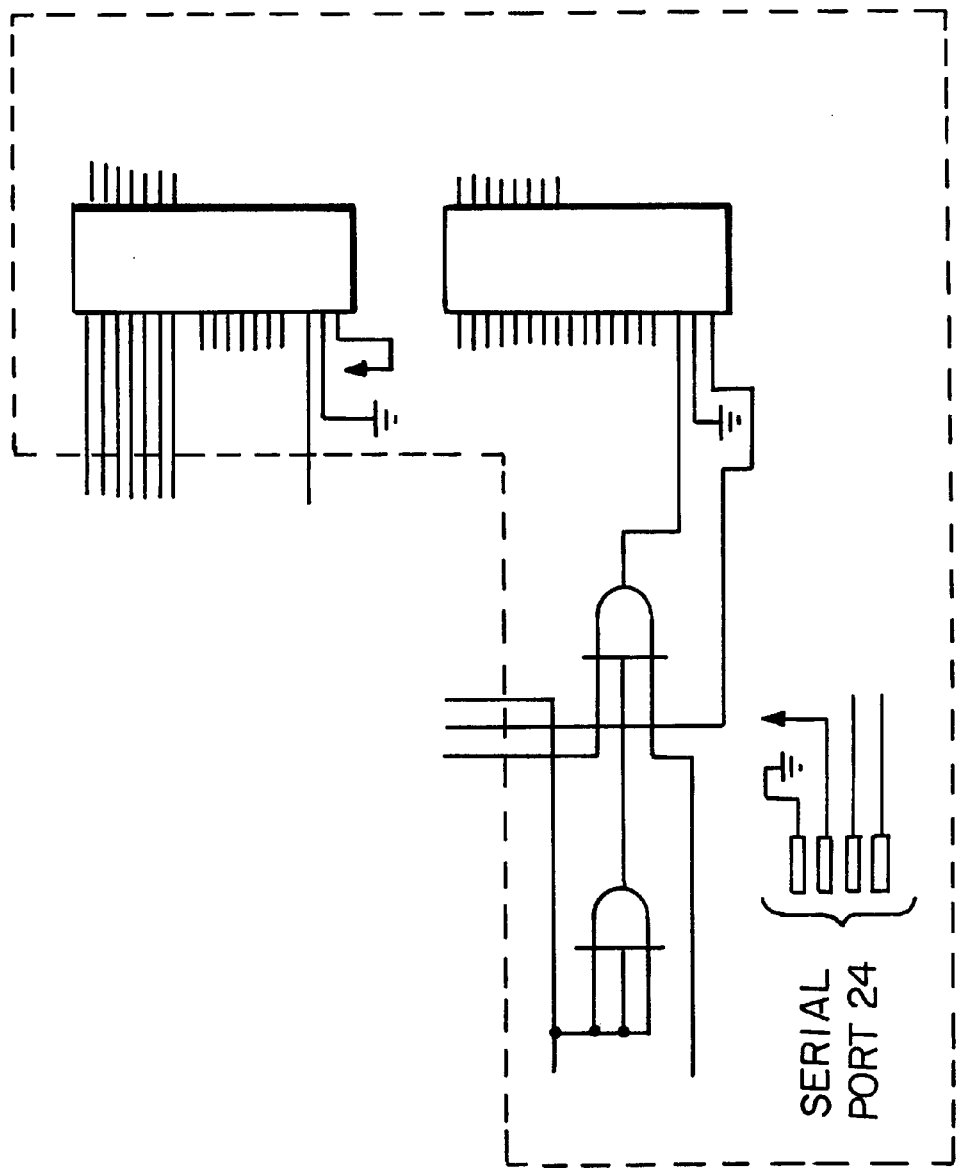
Figure 3F:
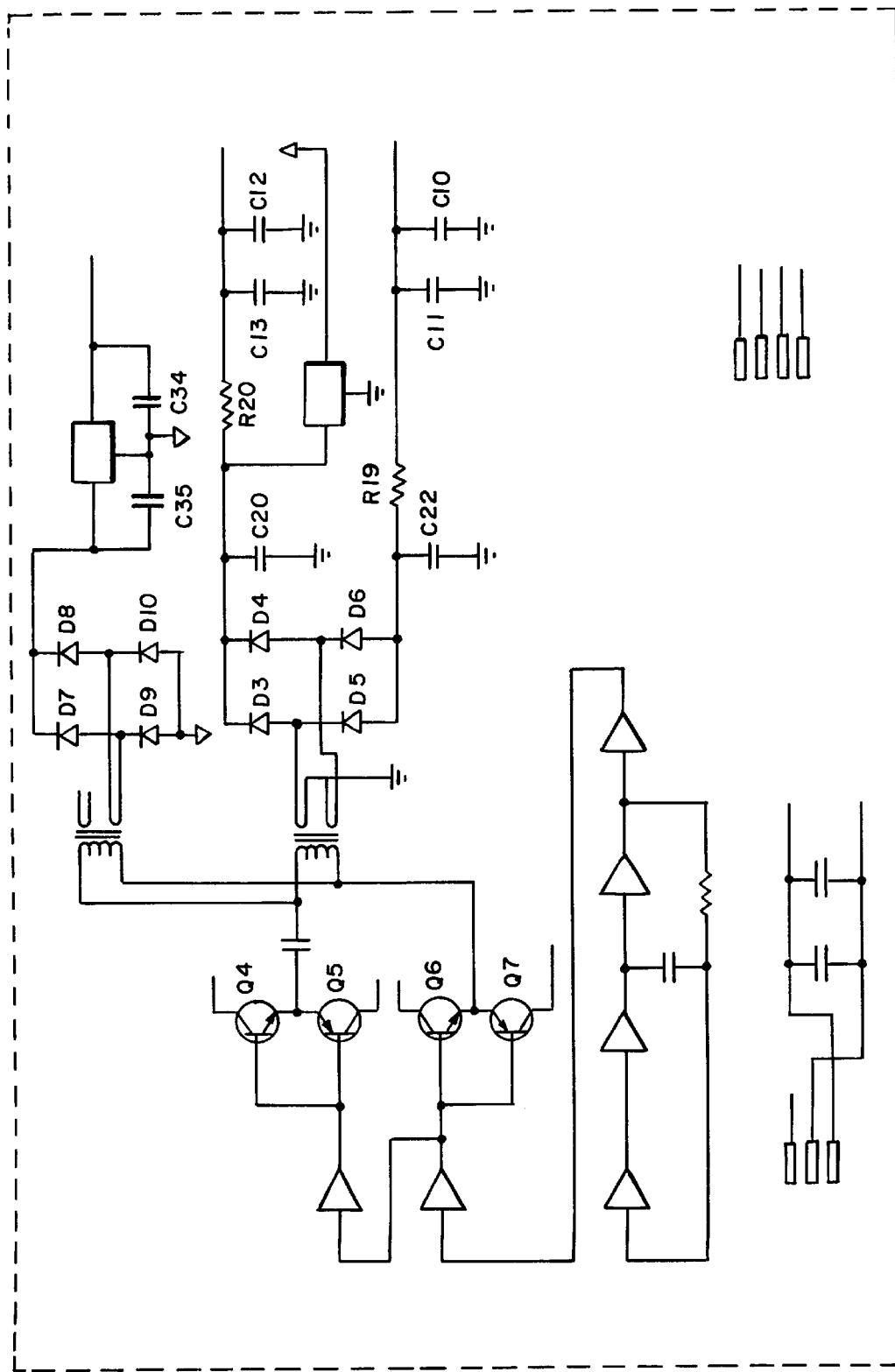

FIG. 2 is a description, in block diagram form, of the hardware used to extract the heart rate from the signal from the hand grip electrodes 1. The hardware illustrated in FIG. 2 is entirely implemented on the heart rate monitor electronics printed circuit board, 3.

The signal 2 from the hand grip electrodes 1 is passed to a physiological amplifier 8 that has differential inputs. The differential input impedance is 88 megohms at low frequencies. This is high compared to electrode impedances. This makes signal amplitude nearly independent of electrode impedance. Common mode signals can cause a differential input if electrode impedance imbalances are significant compared to the differential impedance.

The reference ground 10 of the physiological amplifier 8 is highly isolated from other grounds. The reference ground "floats" relative to the frame of the exercise equipment and everything else. The elements of this isolation include the toroidal transformer 12 in the power supply and the optical isolator 14 which is used to carry pulse width modulated data to the exercise equipment data 22/display system 16. Electrical signals of triboelectric origin are common mode and so change the electrical potential of the reference ground, while only slightly affecting the differential inputs of the differential amplifier. In an alternate embodiment, the reference ground 10 is connected to the exercise machine chassis ground.

The block diagram shows the band pass filter 18 and the differential amplifier 21 components of the physiological amplifier 8 to be separate entities. In fact, they are somewhat merged, and filter components are disposed both before and after the differential amplifier. Each frequency-determining element is labeled (in the schematic of FIG. 3) with its appropriate frequency breakpoint in Hz. Each input of the differential amplifier incorporates a low pass and a high pass filter 13 (note the circuit components R9, R10, C41, C5, C4, C6, R7, R8, R12, and R13 in FIG. 3). Placing the high pass filter at the input improves the ability of the amplifier to recover quickly in the case of overloads. The low pass filter is effective at shunting signals from radio and television stations to ground. Otherwise, these signals would tend to be rectified into interfering signals by semiconductor junctions. The resulting demodulated signal could appear to be a physiological signal. The rest of the effective bandpass filter is incorporated in a group of circuit elements 15 (note the circuit components C8, C9, R21, C10, C12, R28 C14, and R32 in FIG. 3) positioned later in the signal path, past the main components of the differential amplifier 8.

Each input is protected by low leakage diodes 11 (note circuit elements Q1, Q2, Q3, and Q4 in FIG. 3) connected to the power supply. These protect against potentially damaging static discharge that may be applied to the electrodes. There is a means 19 (note signals named INJECT+ and INJECT– in FIG. 3) for injecting either common or differential mode signals to the inputs of the physiological amplifier 8. The amplitude, frequency, and phase of the injected signals are under software control. This makes it possible to detect the presence of a person at the electrodes. This also makes it possible to implement self-diagnostics. The means for doing this is explained in the software section.

The currently embodied analog bandpass filter 18 is designed to pass frequencies between 5 and 20 hertz. This frequency range has been shown to carry heart rate information while rejecting part of the myoelectric and triboelectric contributions. Rejecting 60 Hz was a major consideration. Severe analog filtering reduces the information content of the physiological signal, which allows sophisticated digital signal processing to be accomplished without the expense of high-speed processors or dedicated digital signal processing chips.

The QRS complex 5 of an ECG 4 varies somewhat among healthy individuals, but these differences largely disappear after passing through the filter. The heart rate extraction algorithm can be simplified if it only needs to identify one kind of QRS complex. Heart pathologies may have a dramatic effect on the QRS complex, and an alternate QRS template may be required by the heart rate monitor when pathology exists.

The QRS complex 5 of an ECG 4 is about 20 milliseconds long. The analog filter 18 lengthens this to about 100 milliseconds. The QRS event detector algorithm requires that the QRS complex be kept less than 120 milliseconds. A 3 section Butterworth low pass filter was chosen for the main part of the analog filter because it is well damped and because the group delay does not strongly depend on frequency. A less well-damped filter would lengthen the QRS signal unacceptably. The high pass filter is highly damped. A side benefit of this is rapid overload recovery.

One advantage of this invention is that a modest general-purpose microprocessor is adequate for all calculations. A Motorola MC68HC11 microprocessor 20 was chosen for the current embodiment. It contains 8/16 bit instructions, an ADC, several high-resolution timers, an RS-232 port, and a fast multiply instruction. It contains a 32-kilobyte ROM for all software and a 32-kilobyte RAM, which is used for variables and buffers.

The circuit board incorporates an optically isolated pulse width port 22 for communicating with exercise equipment. This port is currently the main link from the heart rate monitor circuit to the exercise machine controller/display board. Its operation is described in detail in the software section.

Also incorporated is an RS-232 port 24 available for diagnostics and software development. The serial port is used only for diagnostics in the currently described embodiment. In future embodiments, the RS-232 port may become the only link to the exercise equipment, supplanting the pulse width modulated link. This would provide a flexible and bi-directional link. The exercise equipment could inform the heart rate extractor program of useful information. This could include the current pedaling rate, the amount of resistance, and the caloric "burn" rate.

An electrically isolated power supply 26 is incorporated on the printed circuit board. Power to run the heart rate monitor comes from the exercise equipment. The power is converted to a high frequency and passed through a small toroidal transformer. The transformer permits excellent electrical isolation between the ground of the physiological amplifier and the ground of the exercise equipment.

The possibility of injecting signals into the physiological inputs under microprocessor control is the key to comprehensive self-diagnostics. The amplitude, frequency, and phase presented to each input can be varied independently. This makes it possible to make gain and frequency response measurements. It is even possible to make common mode rejection measurements.

The pulse width modulated link 22 can be used to communicate the result of a self-diagnostic to the digital display normally for the heart rate. This permits self-diagnostics in the field without special equipment by end users. More comprehensive self-diagnostics are possible if the RS-232 serial port is used.

Figure 4:
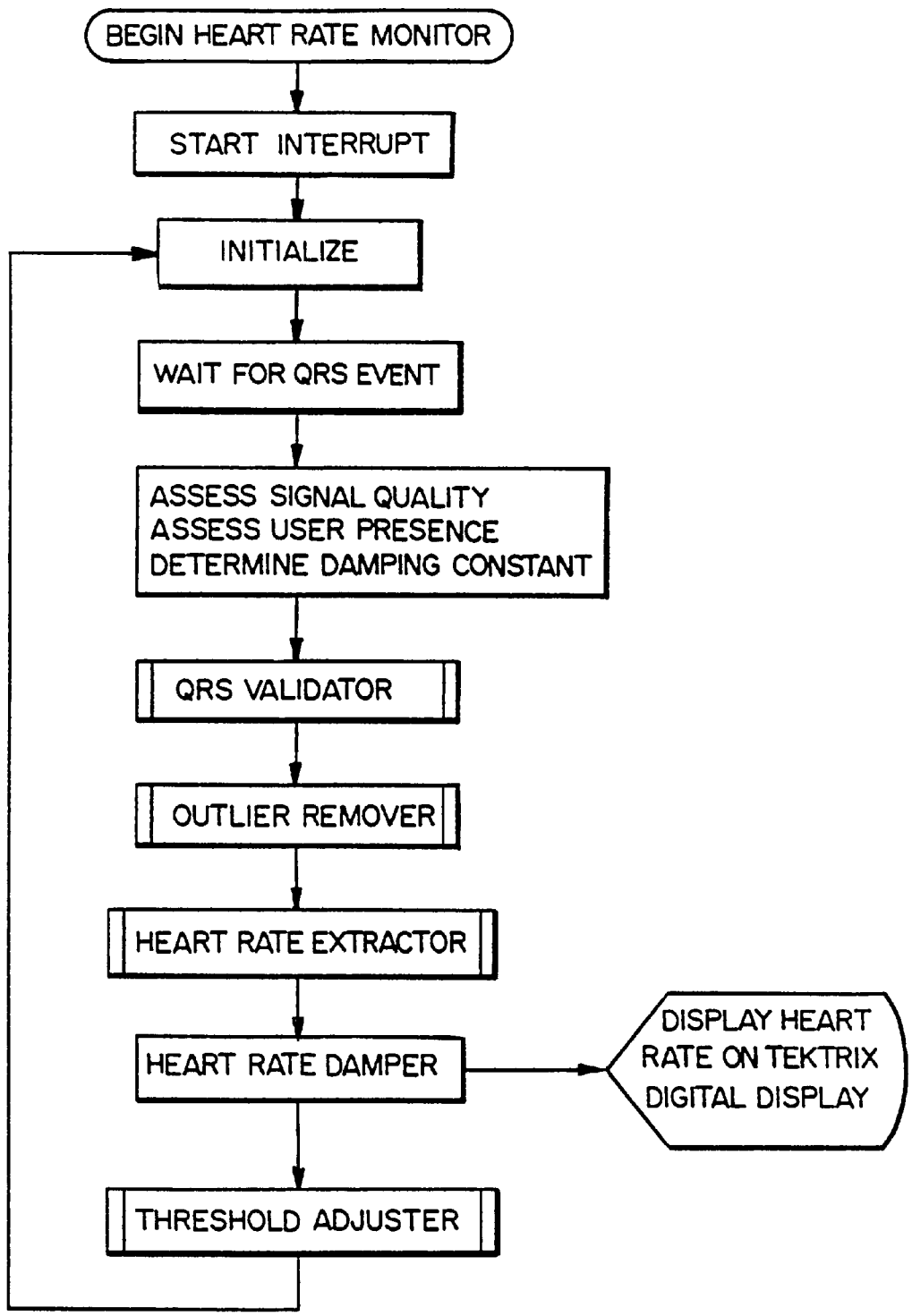
FIG. 4 is a block diagram overview of the entire digital process. The rest of the figures describe in detail the function of the individual blocks in the overview FIG. 4.
Figure 9:
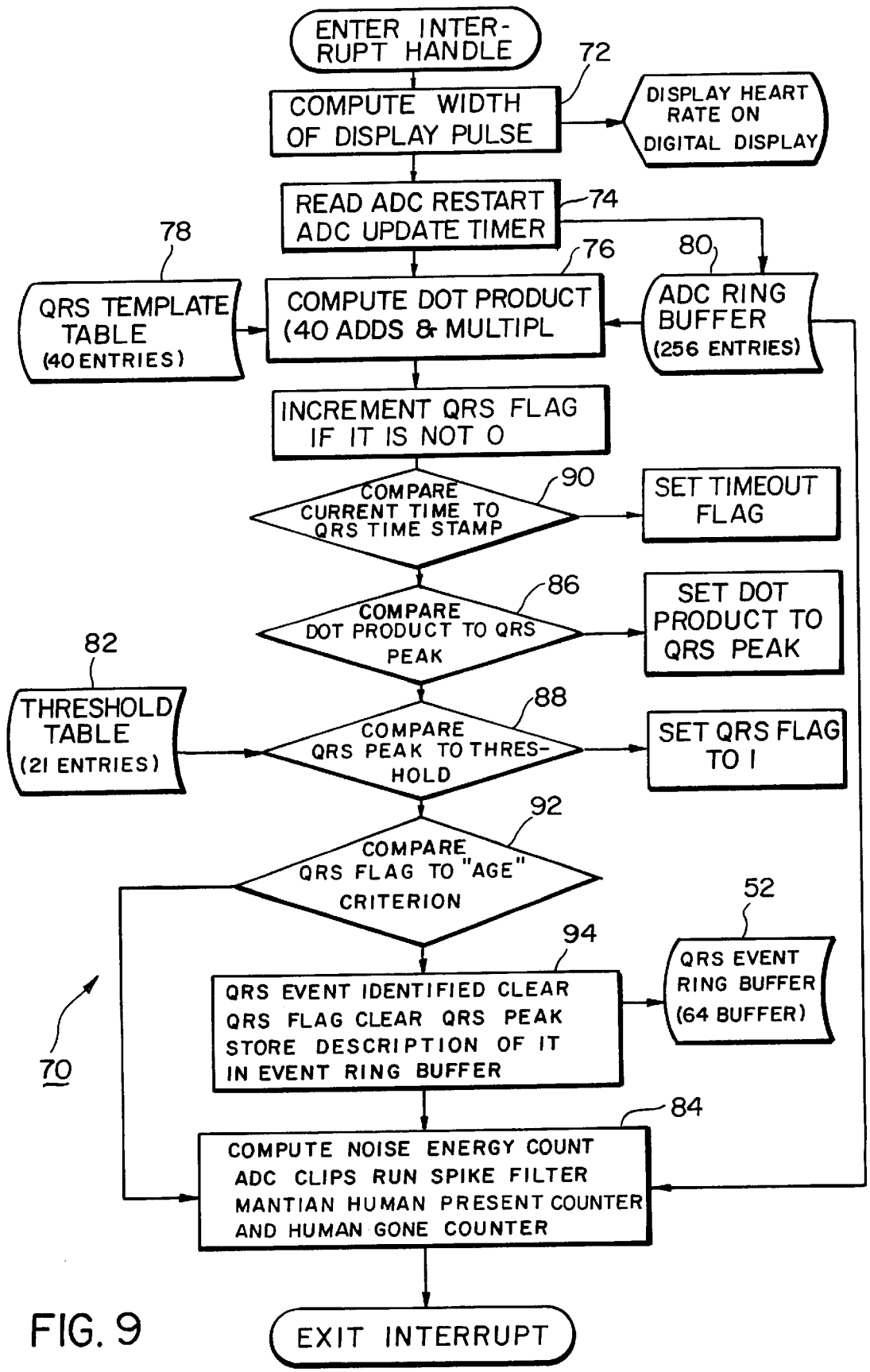
FIG. 9 is a block diagram of the interrupt handler.

FIG. 4 is an overview of the entire software process. Starting at the top of the page of FIG. 4, the interrupt handler 70 (described below with respect to FIG. 9) is invoked by starting the timer 30. Initial values 32 for the damping constant, the QRS intensity threshold, etc. are selected. The process then waits for a QRS event. Note that a QRS event is bound to happen because the interrupt handler produces a "timeout QRS" whenever an implausibly long time interval has passed.

Several parameters 34 are considered in assessing signal quality. These include the severity of ADC clipping, the amount of noise present, the number of rejected events reported by the Heart Rate Extractor, the current heart rate, and the amount of time the person has been at the electrodes. A decision whether to display nothing, dashes, the last known heart rate, or the currently computed heart rate is based these data. A damping constant for the digital heart rate display is also chosen on the basis of signal quality.

The high input impedance and sensitivity of the physiological amplifier 8 is sensitive in surprising ways. For example a person exercising on a nearby machine could introduce a signal that looks like a QRS sequence.

Several methods of detecting a human presence have been devised. They depend on measuring the impedance between the grips. One method, which is heavily dependent on software, involves a "spike" filter. The spike filter algorithm is described in detail in FIG. 9 and its accompanying description. Another method, which is essentially a hardware method, involves a Wheatstone bridge and is described later in this description. The QRS Validator 36, the Outlier Remover 38, the Heart Rate Extractor 40, and the Threshold Adjuster 42 are also described elsewhere in this description.

The damper 44 is important because it determines the "feel" of the display. The heart rate of a real human is chaotic, but people do not want to see the continuously changing digits that reflect this. The heart rate actually sent to the exercise equipment is "damped" in order to make it easier to read. The actual damping algorithm operates on the QRS interval rather than the rate. A new heart rate is computed every time a valid QRS event is detected. This equation has the property that the rate of change with time is constant. This makes the display easier to read. Here it is:

$$Interval_{new} = Interval_{old} + (Interval_{new} - Interval_{old}) * K * Interval_{old}$$

The damping constant, K, can take on one of two values. When myoelectric noise is low, K is set to a high value. This minimizes the time lag in the display. When myoelectric noise is high, K is set to a low value. This prevents the rapid changes in the displayed heart rate and makes the display easier to read. The rate of change also depends on the number of events considered by the Heart Rate Extractor.

Figure 5:
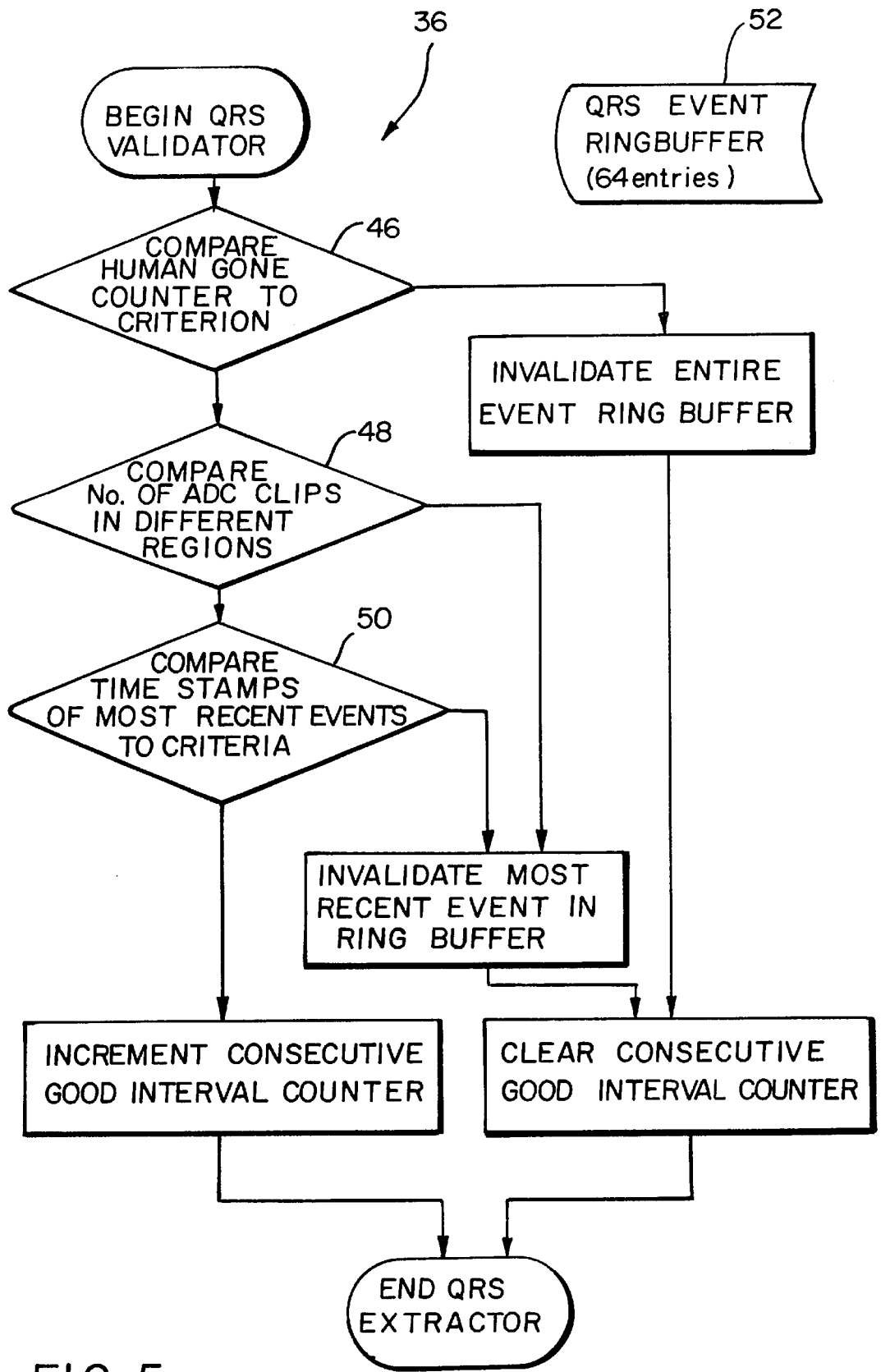
FIG. 5 is a block diagram of the QRS validator/extractor.

The QRS validator 36 (detailed in FIG. 5) operates on the QRS event ring buffer 52. If the Human Gone Counter exceeds a criterion 46, the human is deemed gone and the entire QRS event ring buffer is invalidated. ADC clipping, especially not near the QRS peak is reason 48 to invalidate an event. A good interval counter is maintained. It is a measure of the quality of the data 50 in the QRS event ring buffer 52.

Figure 6:
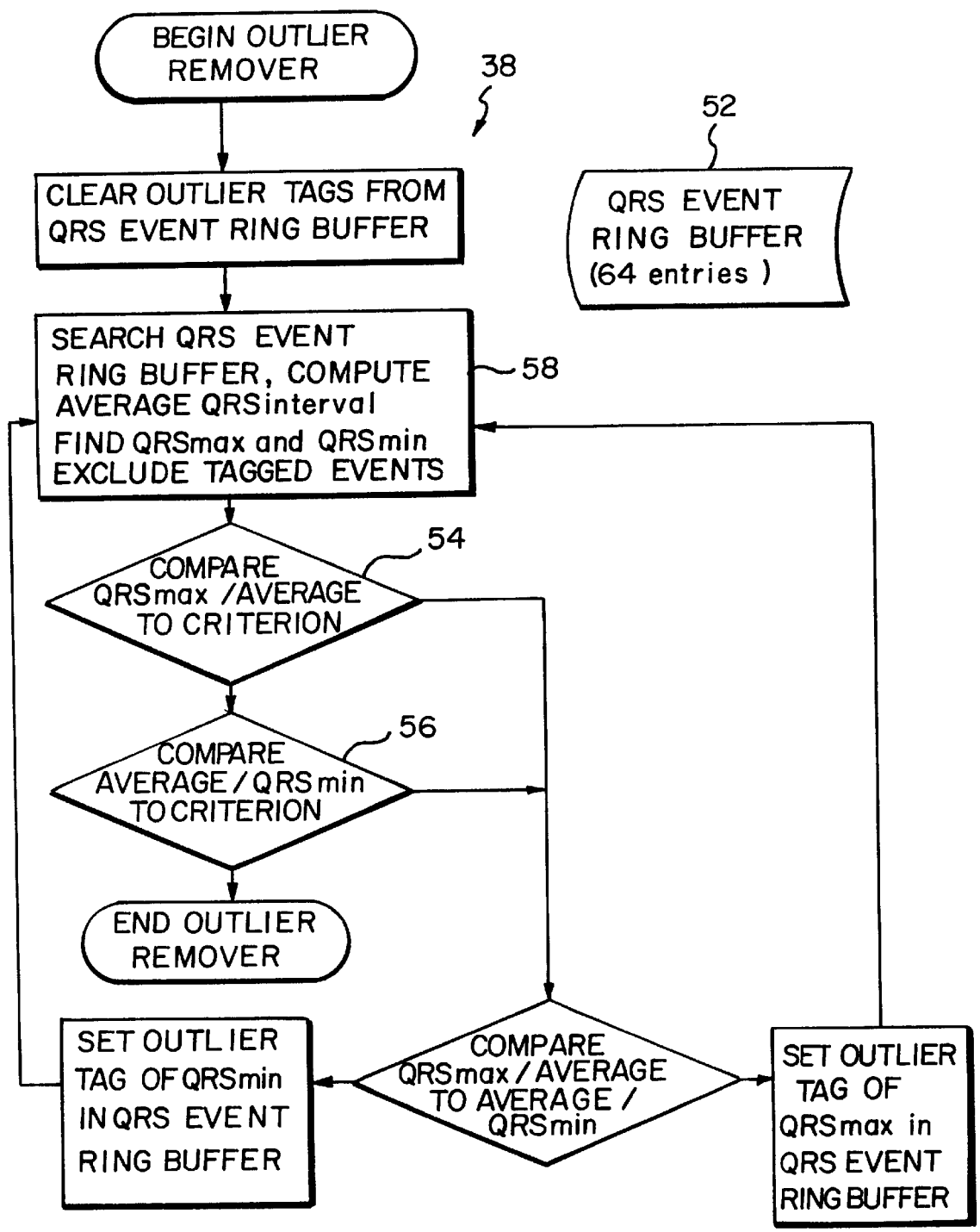
FIG. 6 is a block diagram of the outlier remover.

The Outlier Remover 38 (detailed in FIG. 6) operates on the QRS event ring buffer 52 too. It can make several passes through the ring buffer in order to identify intervals that "stand out from the crowd." Each pass begins by computing the average and identifying the biggest 54 and the smallest 56 interval. The single interval that deviates (in the logarithmic sense) the most from the average is tagged 58 as invalid. This is repeated until no intervals deviate from the average by some criterion. This method is superior to prior art because all of the data, old and new, is examined after every QRS event. It is possible for a previously excluded outlier to contribute to a recent heart rate.

Figure 7:
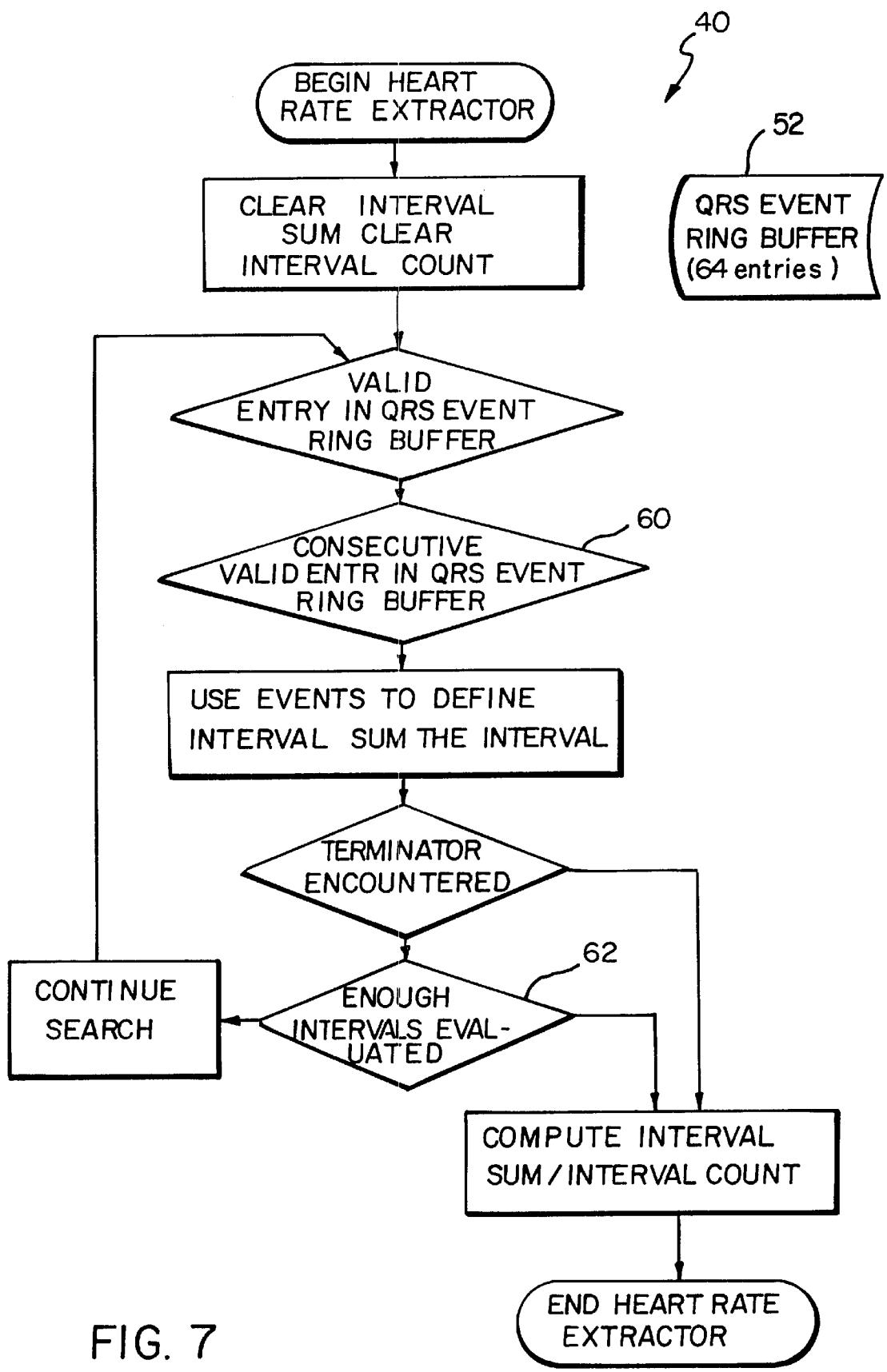
FIG. 7 is a block diagram of the heart rate extractor.

The heart rate extractor 40 (detailed in FIG. 7) also operates on the QRS event ring buffer 52, which now contains events that have been prequalified by the actions of the QRS validator and the outlier remover. In one implementation, the first 33 out of the potential 64 events in the QRS event ring buffer 52 are examined. Only adjacent pairs of qualified events are considered 60. Only the most recent 13 pairs are used in one implementation. The event pairs that are considered may be adjacent, scattered, older, or younger. The raw heart rate is computed from the average of these intervals. In the case where QRS events uncontaminated by noise are available, the heart rate extractor can find enough qualified events in the early part of the QRS ring buffer. In the case of high noise, the whole QRS ring buffer may have to be searched 62. It is claimed that this method of dealing with noisy QRS events is superior to prior art.

Figure 8:
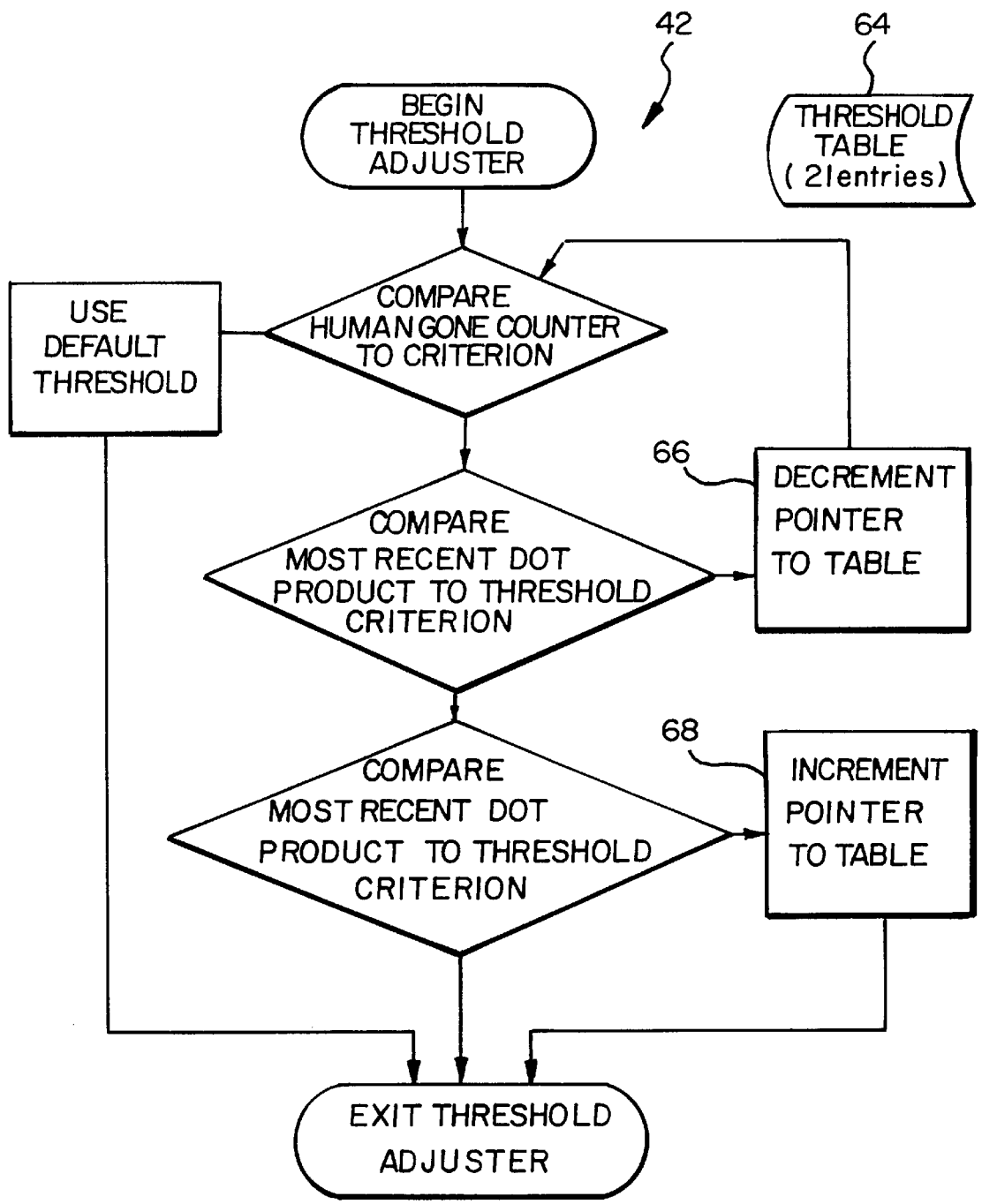
FIG. 8 is a block diagram of the threshold adjuster.

The threshold adjuster 42 (detailed in FIG. 8) can potentially change the threshold after every QRS event. The QRS threshold is currently determined by a table 64 with 21 entries. Successive entries in the table increase by 19 per cent steps. That is to say the spacing is uniform on a logarithmic scale. The range is sufficient to cover a QRS amplitude range of 0.1 to 2 millivolts. In effect, a log is calculated by moving a pointer to a table, which is computationally efficient. This method is claimed to be superior to gain ranging. The heart rate monitor is initialized with the QRS event threshold value set to a value appropriate for a 1 millivolt QRS event. The following circumstances will cause this value to decrease 66 by one step: (a) a person is present and a QRS event timeout has occurred; (b) a person is present, the clip and noise criteria are satisfied, and the amplitude of the current QRS event is less than 1 step (19 per cent) greater than the current threshold.

The following situation will cause the threshold to increase 68: a person is present, the clip and noise criteria are satisfied, and the amplitude of the current QRS event is greater than 4 steps (101 per cent) greater than the current threshold (this may result in a several-step change). The overall effect is to respond to large QRS signals by quickly increasing the threshold, and to respond to small QRS signals by slowly decreasing the threshold. This algorithm is effective at rejecting myoelectric noise while detecting genuine QRS events.

The interrupt handler 70 (detailed in FIG. 9) operates in the background but it does most of the real work in the computational sense. The heart rate monitor currently produces a pulse whenever a QRS event is detected. The width of the pulse encodes the heart rate and other information. The time of occurrence of a pulse is used to flash an icon. The controller/display microprocessor used by Tectrix can conveniently poll at intervals of 278 microseconds. The heart rate monitor microprocessor produces pulses 72 that vary in units of this size. Here is a list of definitions for the various pulse widths: (a) Width=0 unit, heart rate monitor is missing or malfunctioning; (b) Width=2 units, heart rate monitor is functioning and no person is present; (c) Width=4 units, a person is present but the heart rate is unavailable; (d) Width=6 units, a diagnostic sequence has started; (e) Width=8 units, the heart rate monitor has passed the diagnostic and is working correctly, (f) Width=10–38 units, error messages resulting from diagnostics; (g) Width=40 to 220 units, direct integer indication of heart rate in beats per minute.

The pulse interval corresponds to the QRS interval but this does not directly influence the numerical display. Each pulse represents a "raw" QRS event which is used to flash an icon. This visual cue provides feedback to the user. He or she may well respond to the cue by not wiggling the fingers or adjusting the grip on the electrodes in order to give steady icon flashes.

The timer that caused the interrupt is acknowledged 74 and is told to interrupt again in 3.3333 milliseconds. The time stamp counter is incremented. The ADC is restarted and the result becomes the most recent member of the 256 ADC ring buffer 80.

The process of identifying a QRS event starts by computing 76 the dot product from the data in a QRS template table 78 and the most recent entries in the ADC ring buffer 80.

In the present embodiment, the QRS template table 78 comes from a typical and healthy person. It is uncontaminated by myoelectric noise, or noise of any kind. In this sense it is more robust than an autocorrelated model. A dot product is computed after every ADC sample. A large, positive, dot product indicates that a QRS event has occurred. In prior art, the autocorrelation function is used to identify QRS events. In that case, the dot product would be computed from two time records, both of which could be contaminated by myoelectric noise.

The software based peak detector 92 is used to decide: (a) whether a dot product is sufficiently large, (b) whether enough time has passed 90 since the peak occurred. The peak detector depends on two variables. The first is the threshold 82 that the dot product must exceed. The second is the amount of time that must elapse before the QRS event is considered complete. A timer is set to zero whenever dot product exceeds the threshold 88 or a previous peak 86. When this timer reaches a certain count, the QRS is considered complete. The threshold variable is dynamic and it depends on the amplitude of the QRS which varies markedly between individuals. The threshold variable is adjusted by software described elsewhere. The timer variable is fixed in ROM.

At the same time a QRS event is detected 94, several other parameters are computed 84. They are: (a) the total energy in the epoch that precedes the QRS event; (b) the number of times the ADC clipped (was driven to full scale) during the interval over which the dot product was computed; and (c) the number of times the ADC clipped (was driven to full scale) during the epoch that precedes the QRS event. The 64 most recent QRS events candidates are stored in the QRS event ring buffer 52. Each entry contains the following information: (a) the amplitude of the dot product; (b) a time stamp; (c) a noise estimate; (d) a clip count for the QRS event; (e) a clip count for the previous epoch; (f) the current threshold; (g) the time since a person was detected as present; (h) the time since a person was detected as absent; (i) a QRS event missing flag; (j) a QRS event late flag; (k) a QRS event validity flag; and (1) an outlier tag (the interrupt handler does not deal with this).

The human present counter and the human gone counter are maintained by the interrupt handler. Of course this requires a human detector. One human detector is implemented in the following way: a 5-millivolt triangle wave of 37.5 Hz is introduced differentially through 1-nanofarad capacitors at the electrodes. The same capacitors are part of the low pass filter network. At 37.5 Hz these capacitors represent an impedance that is high compared to the impedance between the hands. Gripping the electrodes causes the 37.5 Hz signal to nearly disappear. The microprocessor implements a "spike" filter that detects this frequency in a way that is very efficient in a computational sense. It depends on Nyquist "folding." The 300 sample per second rate of the ADC means that 37.5 Hz folds to zero Hz if every 8th point is summed. The 256 most recent samples divided into 8 groups of 32 each. The first contains sample 1, 8, 16, 24, etc. The second contains 2, 9, 17, 25, etc. the third contains 3, 10, 18, 26, etc., etc. Each group is summed. The result is 8 numbers that describe a single cycle sine wave. The dot product is computed from this sine wave and a stored sine wave. The dot product is large and positive only if the correct frequency and phase is presented. If the dot product fails to exceed a certain criterion, a human is deemed present. This method is superior to prior art because there is minimal disturbance to the normal operation of the electrodes.

An alternative hardware scheme for detecting human presence has been also implemented in an alternate embodiment. It utilizes a DC voltage imposed on the electrodes by Wheatstone bridge with three 50 Kohm resistors, such that a comparator sets a flag when the imposed DC voltage is reduced by conductance between the electrodes. This flag consists of a level that that the interrupt handler can read as "human present".

Although specific, preferred embodiments of the invention have been described, many variations and modifications will be apparent to those skilled in the art. The following claims are intended not only to cover the specific embodiments and methods disclosed, but also to cover the inventive concepts explained herein with the maximum breadth and comprehensiveness permitted by the prior art.

What is claimed is:

1. A heart rate monitor system incorporated in an exercise machine for determining the current heart rate of the user of the machine, comprising:

electrodes in contact with the user's body in order to receive electrocardiographic signals therefrom, such electrocardiographic signals including a QRS complex;

analog circuitry which receives and transfers such electrocardiographic signals as analog signals;

filtering circuitry that produces filtered analog signals containing frequency-limited information regarding the user's QRS complex by substantially limiting the bandwidth of such analog signals to a narrow low-frequency range designed to pass information that is generally found in the QRS complex of most users while limiting myoelectric and triboelectric contributions that tend to be present when the user is operating the exercise machine;

operating circuitry that converts the filtered analog signals into digital signals; and digital circuitry that processes such digital signals against a general model of a QRS complex to provide output signals representing the current heart rate of the user.

2. The heart rate monitor system incorporated in an exercise machine of claim 1 in which the digital circuitry comprises:

measuring circuitry that measures the noise level of the incoming signals; and noise-compensating circuitry that responds to the measuring circuitry in such a way as to provide a slower-speed, more robust output signal when the measuring circuitry indicates a higher noise level of the incoming signals.

3. The heart rate monitor system incorporated in an exercise machine of claim 1 in which the digital circuitry applies wavelet correlation to determine whether the incoming signals represent heart rate signals.

4. The heart rate monitor system incorporated in an exercise machine of claim 3 in which the digital circuitry includes: reconsideration circuitry that permits previously recorded heartbeat events to cause a logically determined heart rate variation from the results of the wavelet correlation.

5. The heart rate monitor system incorporated in an exercise machine of claim 1 in which a tiny low-frequency AC signal is imposed on the monitoring electrodes, and the digital circuitry incorporates a digital spike filter to synchronously detect the absence of this signal as an indicator that a human is present and properly contacting the electrocardiographic electrodes.

6. The heart rate monitor system incorporated in an exercise machine of claim 5 where the human-present indicator signal is utilized to improve the operation of the system by turning the display off when a human is absent.

7. The heart rate monitor system incorporated in an exercise machine of claim 5 where the absence of the human-present indicator signal is utilized to reset the algorithmic parameters to values appropriate for finding and locking onto a new heart rate even when a different human with different ECG parameters appears.

8. The heart rate monitor system incorporated in an exercise machine of claim 1 in which a DC signal is imposed on the monitoring electrodes, and the analog circuitry incorporates a Wheatstone bridge and comparator to detect the absence of this signal as an indicator that a human is present and properly contacting the electrocardiographic electrodes.

9. The heart rate monitor system incorporated in an exercise machine of claim 8 where the human-present indicator signal is utilized to improve the operation of the system by turning the display off when a human is absent.

10. The heart rate monitor system incorporated in an exercise machine of claim 8 where the absence of the human-present indicator signal is utilized to reset the algorithmic parameters to values appropriate for finding and locking onto a new heart rate even when a different human with different ECG parameters appears.

11. The heart rate monitor system incorporated in an exercise machine of claim 1 wherein the narrow low-frequency range is 5 hertz to 20 hertz.

12. A heart rate monitoring method for use in an exercise machine for determining the current heart rate of the user of the machine, comprising the following steps:

using electrodes in contact with the user's body in order to receive electrocardiographic signals therefrom that include a QRS complex;

receiving and transferring such electrocardiographic signals as analog signals with analog circuitry;

filtering the analog signals to produce filtered analog signal containing frequency-limited information regarding the user's QRS complex with circuitry that substantially limits the bandwidth of such analog signals to a narrow low-frequency range designed to pass information that is generally found in the QRS complex of most users while limiting myoelectric and triboelectric contributions that tend to be present when the user is operating the exercise machine;

converting the filtered analog signals into digital signals with appropriate circuitry; and processing such digital signals against a general model of a QRS complex to provide output signals representing the current heart rate of the user.

13. The heart rate monitoring method of claim 12 comprising the following steps:

measuring the noise level of the incoming signals with digital circuitry;

utilizing noise-compensating circuitry which responds to the noise-measuring circuitry in such a way as to provide a slower-speed, more robust output signal when the measuring circuitry indicates a higher noise level of the incoming signals.

14. The heart rate monitoring method of claim 12 in which the digital circuitry applies wavelet correlation to the electrocardiographic signal to determine whether the incoming signals represent heart rate signals.

15. The heart rate monitoring method of claim 14 which additionally causes a logically determined heart rate variation from the results of the wavelet correlation by the use of circuitry which reconsiders the previously-determined validity of previously-recorded heartbeat events.

16. The heart rate monitoring method of claim 12 which imposes a tiny low-frequency AC signal on the monitoring electrodes, and incorporates a digital spike filter to synchronously detect the absence of this signal as an indicator that a human is present and properly contacting the electrocardiographic electrodes.

17. The heart rate monitoring method of claim 16 which utilizes the human-present indicator signal to improve the perceived operation of the system by turning the display off when a human is absent.

18. The heart rate monitoring method of claim 16 which utilizes the absence of the human-present indicator signal to reset the algorithmic parameters to values appropriate for finding and locking onto a new heart rate even when a different human with different ECG parameters appears.

19. The heart rate monitoring method of claim 12 which imposes a DC signal on the monitoring electrodes, and utilizes a Wheatstone bridge and comparator to detect the absence of this signal as an indicator that a human is present and properly contacting the electrocardiographic electrodes.

20. The heart rate monitoring method of claim 19 which utilizes the human-present indicator signal to improve the operation of the system by turning the display off when a human is absent.

21. The heart rate monitor system of claim 19 which utilizes the absence of the human-present indicator signal to reset the algorithmic parameters to values appropriate for finding and locking onto a new heart rate even when a different human with different ECG parameters appears.

22. The heart rate monitoring method of claim 12 wherein the narrow low-frequency range is 5 hertz to 20 hertz.

* * * * *